United States Patent [19]
Wakamatsu et al.

[11] Patent Number: 5,347,035
[45] Date of Patent: Sep. 13, 1994

[54] METHOD FOR CRYSTALLIZING α-L-ASPARTYL-L-PHENYLALANINE METHYL ESTER

[75] Inventors: Hidetoshi Wakamatsu, Eijsden, Netherlands; Tsuneo Harada, Yamaguchi, Japan; Yukio Kunisawa, Yamaguchi, Japan; Kiyotaka Oyama, Yamaguchi, Japan

[73] Assignee: Tosoh Corporation, Yamaguchi, Japan

[21] Appl. No.: 125,193

[22] Filed: Sep. 23, 1993

Related U.S. Application Data

[63] Continuation of Ser. No. 880,732, May 6, 1992, abandoned.

[30] Foreign Application Priority Data

Apr. 13, 1992 [JP] Japan .................................. 4-118464

[51] Int. Cl.$^5$ ............................................ C07C 229/00
[52] U.S. Cl. .................................................. 560/41
[58] Field of Search ........................................ 560/41

[56] References Cited

U.S. PATENT DOCUMENTS 3,833,554  9/1974  Ariyoshi et al. ...................... 560/41
4,994,605  2/1991  Kishimoto et al. .................... 560/41

OTHER PUBLICATIONS

Industrial Crystallization 78, Proceedings of the 7th Symposium on Industrial Crystallization Warsaw, Poland, 25–27 Sep. 1978.

Primary Examiner—José G. Dees
Assistant Examiner—Samuel Barts
Attorney, Agent, or Firm—Cushman, Darby & Cushman

[57] ABSTRACT

A method for crystallizing α-L-aspartyl-L-phenylalanine methyl ester from a hot aqueous solution containing α-L-aspartyl-L-phenylalanine methyl ester by cooling is disclosed, which comprises (i) continuously supplying a hot aqueous solution of α-L-aspartyl-L-phenylalanine methyl ester having a concentration such that the content of L-aspartyl-L-aspartyl-L-phenylalanine methyl esters is less than 0.6% by weight based on the weight of α-L-aspartyl-L-phenylalanine methyl ester in said solution, or if the content of L-aspartyl-L-aspartyl-L-phenylalanine methyl esters is 0.6% by weight or more based on the weight of α-L-aspartyl-L-phenylalanine methyl ester in said solution, to a crystallization vessel the temperature of which is lowered to that corresponding to the solubility of α-L-aspartyl-L-phenylalanine methyl ester or less, and (ii) continuously discharging the formed slurry from the crystallization vessel.

10 Claims, 5 Drawing Sheets

METHOD FOR CRYSTALLIZING α-L-ASPARTYL-L-PHENYLALANINE METHYL ESTER

This is a continuation of application Ser. No. 07/880,732, filed on May 6, 1992.

FIELD OF THE INVENTION

This invention relates to a method for crystallizing α-L-aspartyl-L-phenylalanine methyl ester.

BACKGROUND OF THE INVENTION

α-L-Aspartyl-L-phenylalanine methyl ester (hereinafter referred to as "APM") is a useful dipeptide sweetener which is about 200 times sweeter than sugar. APM can be synthesized by various methods. In any of these methods, after purification, crystallization from a hot aqueous solution by cooling is carried out, and the crystalline product is separated from the slurry obtained by solid-liquid separation, for example, using a centrifugal separator, followed by dehydrating and drying to obtain the final product.

Such crystallization by cooling is usually carried out in a stirring type crystallization vessel provided with a heat transfer surface, or in a crystallization vessel equipped with an external circulation type heat exchanger, or in a crystallization vessel in which cooling is effected only by conductive heat transfer, without providing forced flow for the purpose of improving the crystal properties as described in, for example, JP-A-58-177952. (The term "JP-A" as used herein means an "unexamined published Japanese patent application".)

According to JP-A-58-177952, when APM is crystallized by cooling in a crystallization vessel which is accompanied by forced flow such as stirring and external circulation, there are formed fine crystals which exhibit poor filteration and dehydration properties regardless whether the process is continuous or batchwise. In addition, since these crystals readily deposit onto the heat transfer surface and generate a so-called scale thereby rapidly deteriorating the heat transfer efficiency, the crystallization operation must be frequently interrupted to remove the scale.

In order to avoid such problems, the above-cited patent application proposes a method in which an aqueous APM solution is cooled by conductive heat transfer, without providing forced flow such as mechanical stirring, to form a so-called "pseudo-solid phase", followed by further cooling the system, if desired.

By this method, crystals having improved filtration and dehydration properties in the solid-liquid separation step can be obtained. However, this method is poor in efficiency for cooling since the cooling by conductive heat transfer is carried out without stirring and continued even after the "pseudo-solid phase" has been formed.

Such is disadvantageous in the case of crystallizing a substance like APM which is easily decomposed by heat to form non-sweet 5-benzyl-3,6-dioxo-2-piperazine acetic acid (hereinafter referred to as "DKP") and α-L-aspartyl-L-phenylalanine (hereinafter referred to as "AP").

According to this method, crystallization vessels which are generally used on an industrial scale, such as a vessel type crystallizer, cannot be used, but only special crystallization vessels provided with a large heat transfer surface, from which the "pseudo-solid phase" can be discharged, as proposed in JP-A-58-177952, can be used. As a matter of course, such crystallization vessels are not only poor in cooling efficiency but also expensive, and the crystallization method therefore has disadvantages as an industrial crystallization method.

In order to solve the above-described problems encountered in conventional crystallization methods of APM, the present inventors made extensive and intensive investigations. As a result, it was found that APM is decomposed in a hot aqueous solution to form α-L-aspartyl-L-aspartyl-L-phenylalanine methyl ester and β-L-aspartyl-L-aspartyl-L-phenylalanine methyl ester (the former being hereinafter referred to as "α-A₂PM", the latter as "β-A₂PM", and the both as "A₂PM", respectively), in addition to DKP and AP which have hitherto been known to be formed. As a result of further investigations, it was also found that though among these compounds, DKP and AP do not substantially affect the crystallization behavior of APM, A₂PM causes so-called crystallization inhibition and extremely adversely affects the crystallization behavior of APM.

The inventors made still further investigations based on this finding. As a result, it was found that if crystallization of APM is continuously carried out by cooling while maintaining the content of A₂PM at a certain level, APM crystals having good filtration and dehydration properties can be formed without substantially generating a scale on the wall and heat transfer surface of a crystallization vessel, under forced flow conditions such as mechanical stirring (see JP-A-3-106899 of some of the present inventors, where this level preliminarily has been described as 150 ppm or less).

SUMMARY OF THE INVENTION

The object of this invention is to provide an improved method for crystallizing APM, which makes it possible to obtain APM crystals having good filtration and dehydration properties.

This invention relates to a method for crystallizing α-L-aspartyl-L-phenylalanine methyl ester from a hot aqueous solution containing α-L-aspartyl-L-phenylalanine methyl ester by cooling, which comprises (i) continuously supplying a hot aqueous solution of α-L-aspartyl-L-phenylalanine methyl ester having a concentration such that the content of L-aspartyl-L-aspartyl-L-phenylalanine methyl esters is less than 0.6% by weight based on the weight of α-L-aspartyl-L-phenylalanine methyl ester in said solution, or if the content of L-aspartyl-L-aspartyl-L-phenylalanine methyl esters is 0.6% by weight or more based on the weight of α-L-aspartyl-L-phenylalanine methyl ester in said solution, the concentration of L-aspartyl-L-aspartyl-L-phenylalanine methyl esters in said solution is 150 ppm by weight or less, to a crystallization vessel the temperature of which is lowered to that corresponding to the solubility of α-L-aspartyl-L-phenylalanine methyl ester or less, and (ii) continuously discharging the formed slurry from the crystallization vessel.

DETAILED DESCRIPTION OF THE INVENTION

By the method of this invention, APM crystals having good filtration and dehydration properties can be produced under forced flow conditions such as mechanical stirring. This is quite surprising in view of the crystallization behavior of APM which has been reported such that no improvements in the crystal properties of APM can be attained under forced flow conditions such as stirring, irrespective of any other conditions and operations employed [Kishimoto and Naruse, *Chemistry and Industry*, pp. 127–128 (Feb. 16, 1987) and *Journal of Chemical Technology and Biotechnology*, Vol. 43, pp. 71–82 (1988)].

It is known that $A_2PM$ which by the present invention has been found to cause crystallization inhibition of APM is formed in a large amount as a by-product of APM in the condensation reaction between a strong acid adduct of aspartic acid anhydride and L-phenylalanine methyl ester (JP-A-49-7245).

As described hereinabove, the present inventors have found that $A_2PM$ is also formed when an aqueous APM solution is exposed to a high temperature for an extended period of time. In this case, $A_2PM$ is formed as a mixture of $\alpha$-$A_2PM$ and $\beta$-$A_2PM$ at a ratio of from 3/1 to 5/1. When such a mixture is subjected to high-performance liquid chromatography under conditions set forth below, there are found peaks at a retention time of 40 minutes and 30 minutes, respectively. These compounds were each collected from the respective peaks and identified by mass spectrometry, proton NMR, and $C^{13}$-NMR. The compounds were also confirmed by comparing with separately chemically synthesized authentic samples.

Condition of High-Performance Liquid Chromatographic Analysis

Apparatus: High-Performance Liquid Chromatograph CCPM (manufactured by Tosoh Corporation)

Column: TSK Gel G 2000SW (manufactured by Tosoh Corporation) 7.5 mm (internal diameter)×600 mm Mobile phase: $CH_3CN/H_2O = 8/2 + 5$ mM-$KH_2PO_4$ (pH=6.1)

Flow rate: 1.6 ml/min.

Pressure: 32 kg/cm$^2$

Detector: UV-8000 (manufactured by Tosoh Corporation)

Figure 1:
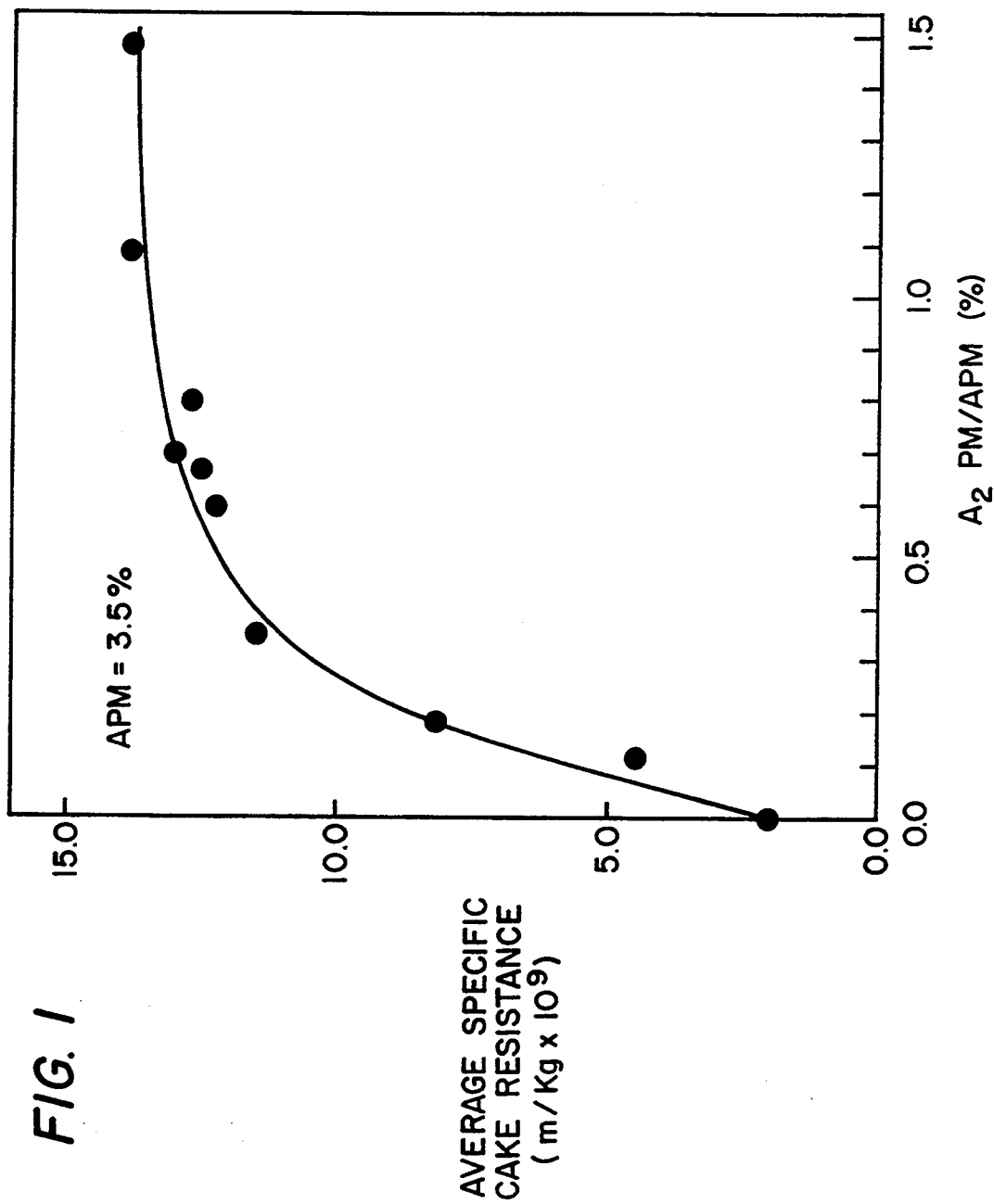
FIG. 1 is a graph showing the relationship between the weight ratio of A₂PM to APM in an aqueous APM solution having an APM concentration of 3.5% and the average specific cake resistance of the APM slurry.
Figure 2:
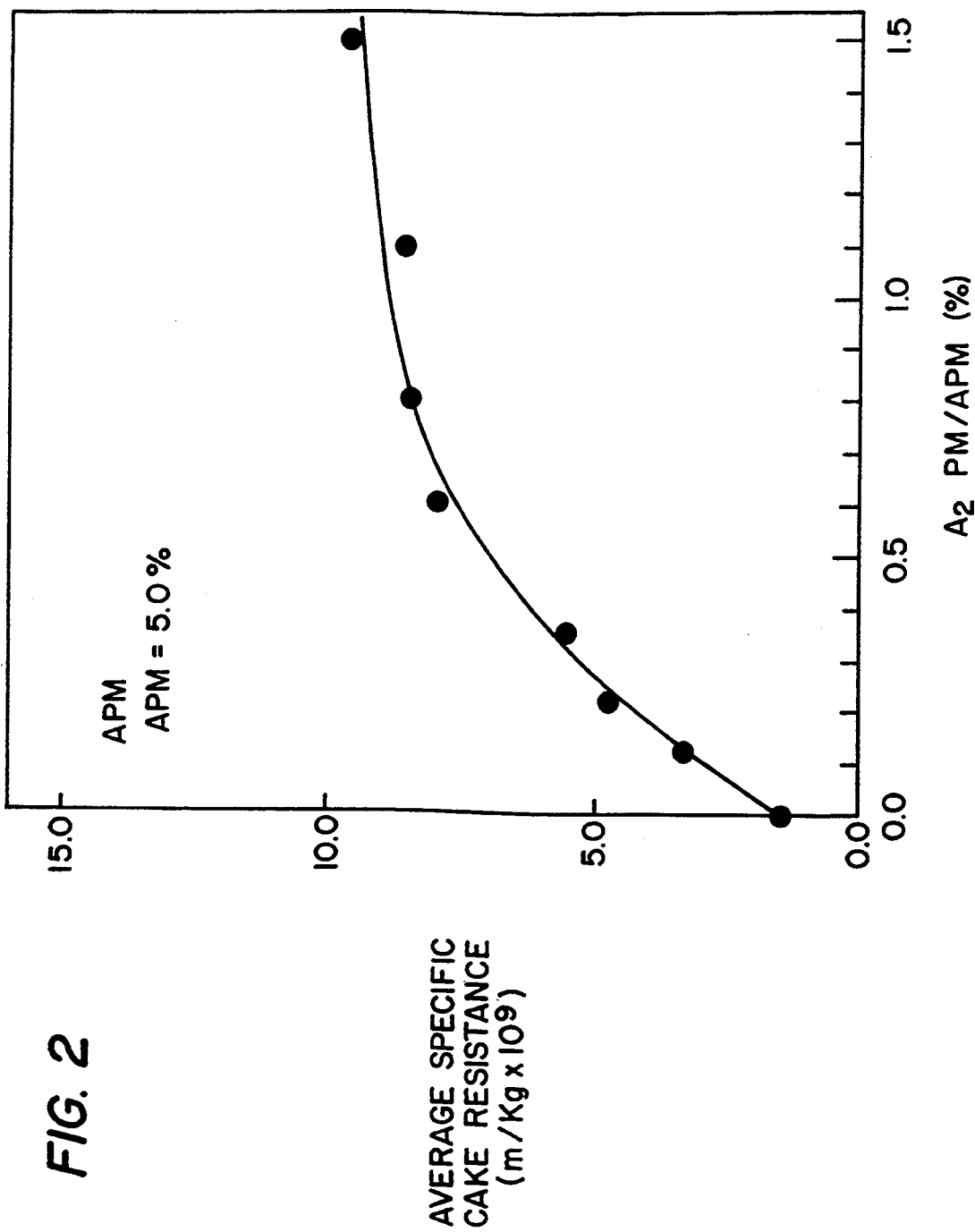
FIG. 2 is a graph showing the relationship between the weight ratio of A₂PMs to APM in an aqueous APM solution having an APM concentration of 5.0% and the average specific cake resistance of the APM slurry.

As a result of various investigations regarding the influence of $A_2PM$ on the crystallization of APM (see Examples 1 to 17 and Comparative Examples 1 to 8), the results as shown in FIGS. 1 and 2 were obtained. It can be understood from these figures that the content of $A_2PM$ (the sum of $\alpha$-$A_2PM$ and $\beta A_2PM$) should be less than 0.6% by weight, preferably 0.35% by weight or less based on the weight of APM. Further, if the content of $A_2PM$ is 0.6% by weight or mor based on the weight of APM, the concentration of $A_2PM$ in the aqueous solution should be 150 ppm by weight or less, preferably 100 ppm by weight or less.

As described above, a large amount of $A_2PM$ is formed in the chemical synthesis of APM (JP-A-49-7245). Further, the amount of formation of $A_2PM$ in an aqueous APM solution is proportional to the period of time when the solution is exposed to a high temperature (see FIG. 4 and Reference Example). Accordingly, in order to crystallize APM from an aqueous APM solution having a low $A_2PM$ content (<0.6 by weight relative to APM), it is desired not to expose the solution to a high temperature for a long period of time. For example, in the case of a hot aqueous solution at 60° C., the exposure time should be about 20 hours or shorter, and in the case of a hot aqueous solution at 70° C., the exposure time should be about 5 hours or shorter.

Even when $A_2PM$ is once formed, such is accepted if $A_2PM$ can be sufficiently removed from the aqueous APM solution.

Ion exchange resins and ion exchange membranes having anion exchanging groups can be used for the removal of $A_2PM$ from the solution.

In this invention, the crystallization is carried out by continuously supplying a hot APM-containing aqueous solution into a crystallization vessel and continuously cooling it while continuously discharging the slurry containing APM crystals. The temperature of the hot APM-containing aqueous solution is usually in the range of from 30° to 100° C., and preferably from 30° to 80° C., taking into consideration the fact that APM is partially decomposed to form $A_2PM$ at higher temperatures.

In this invention, the crystallization vessel may utilize forced flow, in addition to the flow conditions resulting from the supply of the hot aqueous APM solution and the discharge of the slurry containing APM crystals. Forced flow can be generated by a stirrer provided in the crystallization vessel. External circulation by a pump can also be employed.

APM crystals deposited in accordance with the method of this invention are in the form of so-called "bundle-like aggregates", which may vary in average thickness according to any applied external stress or forced flow and the time of such conditions. In the case of forced flow by a stirrer, the stirring is preferably relatively gentle. However, if the stirring is too gentle, the deposition of APM crystals on the heat transfer surface of the crystallization vessel becomes remarkable; therefore, it is necessary to select an appropriate stirring speed.

Accordingly, the rotational speed of the stirrer is chosen such that the tip speed of stirrer blades is in the range of from 0.5 to 5 m/sec., and more preferably from 1.0 to 4 m/sec.

The continuous crystallization method according to this invention also can be carried out by continuously supplying a hot APM-containing aqueous solution into a crystallization vessel provided with an external jacket or external circulation type heat exchanger to be cooled by passing a cooling medium therethrough, and continuously discharging the APM slurry.

The average temperature of the contents of the crystallization vessel may be varied depending on the temperature of the aqueous APM solution supplied. In general, it is from 0° to 40° C., preferably from 0° to 30° C., and more preferably from 0° to 20° C.

The aqueous APM solution supplied must reside in the crystallization vessel for a period of time sufficient to resolve the supersaturation of APM. Since the inside of the crystallization vessel is already cooled, and a large amount of APM crystals are present therein, the supersaturation will be relatively rapidly resolved, and a relatively short residence time is required for the aqueous APM solution in the crystallization vessel. Accordingly, the residence time of the aqueous APM solution in the crystallization vessel is mainly determined by the cooling capacity. An excessively long residence time is not desirable since the APM crystals formed according to the method of this invention tend to become smaller as the residence time increases. The residence time of the aqueous APM solution in the crystallization vessel is usually in the range of from several minutes to 15 hours, preferably to less than 10 hours, and more preferably to less than 5 hours.

The APM slurry discharged from the crystallization vessel is further cooled, if desired. Thereafter, the crystals are separated from the mother liquor by means of a solid-liquid separator and then dried to give the final product. As the solid-liquid separator, any solid-liquid separator which is conventionally used in the industry, inclusive of centrifugal separators, vacuum filters, and pressure filters, can be employed.

The hot APM-containing aqueous solution of APM used in this invention may contain, in addition to water, one or more organic solvents. The concentration of APM in the APM-containing aqueous solution must be the solubility of APM or less at the feed temperature and above the solubility of the solution after cooling. Accordingly, the concentration of APM in the solution will be in the range of from 1.5 to 8% in the case where the solvent is water, and it may be varied depending on the temperature of the solution.

This invention will further be explained by way of the following examples. It is needless to say that the invention is by no means limited by these examples.

In the examples, the average specific resistance of the cake obtained by filtration of the slurry (specific cake resistance) was determined in the following way.

That is, by using a suction filter (leaf tester) fitted with a polypropylene filter cloth having an air permeability of 5 ml/cm$^2$·sec (12 mmH$_2$O), 1,000 ml of a slurry containing APM crystals formed by cooling was filtered at −400 mmHg, while pouring the slurry such that the filtration was performed continuously without drying up of the slurry on the filter cloth. The average specific cake resistance ($\alpha$) was calculated from the period of time [t (sec)] lapsed from the start to the completion of the filtration (the filtration was considered complete when the solvent of the slurry no longer remained on the filter cloth) and from the change in the volume of the filtrate [V (m$^3$)] with the lapse of time, in accordance with the following equation:

$$\alpha = (m \cdot 2 \cdot \Delta P \cdot A^2)/(c \cdot \eta) \ (m/kg)$$

wherein:
m = t/V$^2$ − n/V (sec/m$^6$)
n = (Rm·$\eta$/$\Delta$P·A) (sec/m$^3$)
Rm: Specific resistance of filter cloth (5.5×10$^9$) (m$^{-1}$)
$\eta$: Viscosity of filtrate (=1.52×10$^{-3}$) (Pa·sec)
$\Delta$P: Pressure [400 mmHg (53,329 Pa)]
A: Filtration area [1/127.3(m$^2$)]
C: Weight of dried APM per unit volume of filtrate (kg-dry APM/m$^3$ of filtrate)

It can be understood from the above equation that since the average specific cake resistance ($\alpha$) is proportional to the time (t) lapsed from the start to the completion of the filtration, APM crystals having better filtration properties give a lower average specific cake resistance.

Further, as another evaluation method for the filtration properties, the filtration speed of the slurry was measured in the following way.

That is, by using a suction filter (leaf tester) fitted with a polypropylene filter cloth having an air permeability of 5 ml/cm$^2$·sec (12 mmH$_2$O), 500 ml of a slurry containing APM crystals formed by cooling was filtered at −400 mmHg, while pouring the slurry such that the filtration was performed continuously with no drying up of the slurry on the filter cloth. The filtration speed of the sample was calculated from the period of time lapsed from the start to the completion of the filtration (the filtration was considered complete when the solvent of the slurry no longer remained on the filter cloth) and the volume of the filtrate at that time.

EXAMPLE 1

Into a glass crystallization vessel (internal volume: 2,500 ml) equipped with an external cooling jacket and a stirrer, 2,000 ml of an aqueous solution (60° C.) containing 3.5% of APM and 123 ppm of A$_2$PM (A$_2$PM/APM=0.35%) was charged. While stirring at a tip speed of the stirrer blades of 1.36 m/sec., the temperature in the crystallization vessel was lowered at a rate of 5° C./10 min. by passing a cooling medium from an external water bath through the jacket, to obtain an APM slurry solution. After the temperature in the crystallization vessel had reached 5° C., continuous crystallization was carried out in the following manner.

That is, a 3.5% aqueous APM solution containing 123 ppm of A$_2$PM (A$_2$PM/APM=0.35%) kept in an external constant temperature bath maintained at 60° C. was continuously fed into the crystallization vessel containing the previously prepared APM slurry, which was maintained at 5° C. by means of a cooling medium, by a pump at such a rate that the residence time of the solution was 2 hours, and at the same time, the formed slurry was continuously discharged at the same rate.

The filtration speed of the discharged slurry was determined by a leaf tester. As a result, it showed an almost constant value when the solution in the crystallization vessel had been substituted about 6 times or more. Thereafter, the continuous crystallization was continued, and the specific cake resistance of the discharged slurry was determined at the time when the solution in the crystallization vessel had been substituted 10 times. At this time, the determined specific cake resistance was 11.5×10$^9$ m/kg.

In the subsequent examples, the specific cake resistance was determined at the time when the solution in the crystallization vessel had been substituted 10 times.

EXAMPLE 2

One mole of N-benzyloxycarbonyl-L-aspartic acid anhydride was reacted with 1 mole of APM in 300 g of acetic acid at room temperature for 24 hours, to obtain 290 g of N-benzyloxycarbonyl-L-aspartyl-L-aspartyl-L-phenylalaninemethyl ester (Z-A$_2$PM, $\alpha/\beta$=4/1).

The thus obtained Z-A$_2$PM was catalytically reduced in methanol in the presence of a palladium-on-carbon catalyst in a customary manner. After the catalyst had been removed by filtration, the methanol was distilled off to obtain 210 g of A$_2$PM ($\alpha/\beta$=4/1).

The thus prepared A₂PM was added to a hot aqueous solution containing 3.5% of APM, to prepare a hot APM-containing aqueous solution (A₂PM/APM=0.6%, A₂PM=210 ppm). The solution was then subjected to continuous crystallization, and the average specific cake resistance of the resulting slurry was determined, in the same manner as in Example 1.

EXAMPLE 3

A₂PM was obtained under the same conditions as in Example 2 and added to a hot aqueous solution containing 5.0% of APM, to prepare a hot aqueous APM solution (A₂PM/APM=0.35%, A₂PM=123 ppm). The solution was then subjected to continuous crystallization, and the average specific cake resistance of the resulting slurry was determined, in the same manner as in Example 1.

EXAMPLE 4

A₂PM was obtained under the same conditions as in Example 2 and added to a hot aqueous solution containing 5.0% of APM, to prepare a hot aqueous APM solution (A₂PM/APM=0.6%, A₂PM=300 ppm). The solution was then subjected to continuous crystallization, and the average specific cake resistance of the resulting slurry was determined, in the same manner as in Example 1.

COMPARATIVE EXAMPLE 1

A₂PM was obtained under the same conditions as in Example 2and added to a hot aqueous solution containing 3.5% of APM, to prepare a hot aqueous APM solution (A₂PM/APM=0.8%, A₂PM=280 ppm). The solution was then subjected to continuous crystallization, and the average specific cake resistance of the resulting slurry was determined, in the same manner as in Example 1.

COMPARATIVE EXAMPLE 2

A₂PM was obtained under the same conditions as in Example 2 and added to a hot aqueous solution containing 3.5% of APM, to prepare a hot aqueous APM solution (A₂PM/APM=1.10%, A₂PM=385 ppm). The solution was then subjected to continuous crystallization, and the average specific cake resistance of the resulting slurry was determined, in the same manner as in Example 1.

COMPARATIVE EXAMPLE 3

A₂PM was obtained under the same conditions as in Example 2 and added to a hot aqueous solution containing 3.5% of APM, to prepare a hot aqueous APM solution (A₂PM/APM=1.50%, A₂PM=525 ppm). The solution was then subjected to continuous crystallization, and the average specific cake resistance of the resulting slurry was determined, in the same manner as in Example 1.

COMPARATIVE EXAMPLE 4

A₂PM was obtained under the same conditions as in Example 2 and added to a hot aqueous solution containing 5.0% of APM, to prepare a hot aqueous APM solution (A₂PM/APM=0.8%, A₂PM=400 ppm). The solution was then subjected to continuous crystallization, and the average specific cake resistance of the resulting slurry was determined, in the same manner as in Example 1.

COMPARATIVE EXAMPLE 5

A₂PM was obtained under the same conditions as in Example 2 and added to a hot aqueous solution containing 5.0% of APM, to prepare a hot aqueous APM solution (A₂PM/APM=1.10%, A₂PM=550 ppm). The solution was then subjected to continuous crystallization, and the average specific cake resistance of the resulting slurry was determined, in the same manner as in Example 1.

COMPARATIVE EXAMPLE 6

A₂PM was obtained under the same conditions as in Example 2 and added to a hot aqueous solution containing 5.0% of APM, to prepare a hot aqueous APM solution (A₂PM/APM=1.50%, A₂PM=750 ppm). The solution was then subjected to continuous crystallization, and the average specific cake resistance of the resulting slurry was determined, in the same manner as in Example 1.

EXAMPLE 5

Into a glass cylindrical column (inner diameter: 40 mm) equipped With an external jacket, 250 ml of a strongly basic anion exchange resin of Cl⁻ type (Amberlite IRA-410, a trade mark by Rohm & Haas Co.) was charged.

While circulating hot water at 60° C. through the external jacket, 2 liters of an aqueous solution (60° C.) containing 123 ppm of A₂PM, 3.6% of APM, 0.012% of DKP and 0.005% of AP was passed downward through the column at a space velocity of 3.0 hr⁻¹, to obtain a solution containing 3.5% of APM, 0.004% of DKP, 0.0006% of AP and 0 ppm of A₂PM.

This solution was placed in a glass crystallization vessel (internal volume: 2,500 ml) equipped with an external cooling jacket and a stirrer. While stirring at a tip speed of the stirrer blades of 1.36 m/sec., the temperature in the crystallization vessel was lowered at a rate of 5° C./10 min. by passing a cooling medium from an external water bath through the jacket, to obtain an APM slurry solution. After the temperature in the crystallization vessel had reached 5° C., continuous crystallization was carried out in the following manner.

That is, an aqueous solution (60° C.) containing 123 ppm of A₂PM, 3.6% of APM, 0.012% of DKP and 0.005% of AP was continuously fed into the same ion exchange resin column as described above by a pump at such a rate that the residence time of the solution in the crystallization vessel was 2 hours, to thereby completely remove A₂PM. The resulting solution was continuously charged into a crystallization vessel containing the previously prepared APM slurry, which was maintained at 5° C. by means of a cooling medium, and at the same time, the formed slurry was continuously discharged. During this operation, two ion exchange resin columns were prepared, and before breakthrough of A₂PM took place, it was switched to a new one, while the used column was regenerated.

The filtration speed of the discharged slurry was determined by a leaf tester. As a result, it showed an almost constant value when the solution in the crystallization vessel had been substituted about 6 times or more. Thereafter, the continuous crystallization was continued, and the specific cake resistance of the discharged slurry was determined at the time when the solution in the crystallization vessel had been substituted 10 times. At this time, the determined specific cake resistance was $2.1 \times 10^9$ m/kg.

In the subsequent examples, the specific cake resistance was determined at the time when the solution in the crystallization vessel had been substituted 10 times.

EXAMPLE 6

Into a glass cylindrical column (inner diameter: 80 mm) equipped with an external jacket, 5,000 ml of a strongly basic anion exchange resin of Cl$^-$ type (Amberlite IRA-410, a trade mark by Rohm & Hass Co.) was charged. While circulating hot water of 60° C. through the external jacket, 20 l of a solution (60° C.) containing 250 ppm of A$_2$PM, 3.6% of APM, 0.20% of DKP and 0.06% of AP (this solution was prepared based on the results of Reference Example) was passed downward through the column at a space velocity of 2.5 hr$^{-1}$, to obtain a solution containing 3.5% of APM, 0.05% of DKP, 0.03% of AP and 60 ppm of A$_2$PM (A$_2$PM/APM=0.17%).

The resulting solution was subjected to continuous crystallization in the same manner as in Example 1, to obtain a slurry having an average specific cake resistance of $8.3 \times 10^9$ m/kg.

COMPARATIVE EXAMPLE 7

The solution used in Example 6 (A$_2$PM/APM=0.69%, A$_2$PM=250 ppm) was subjected to continuous crystallization, without being subjected to the ion-exchange resin treatment, to obtain a slurry having an average specific cake resistance of $13.1 \times 10^9$ m/kg.

EXAMPLE 7

Figure 3:
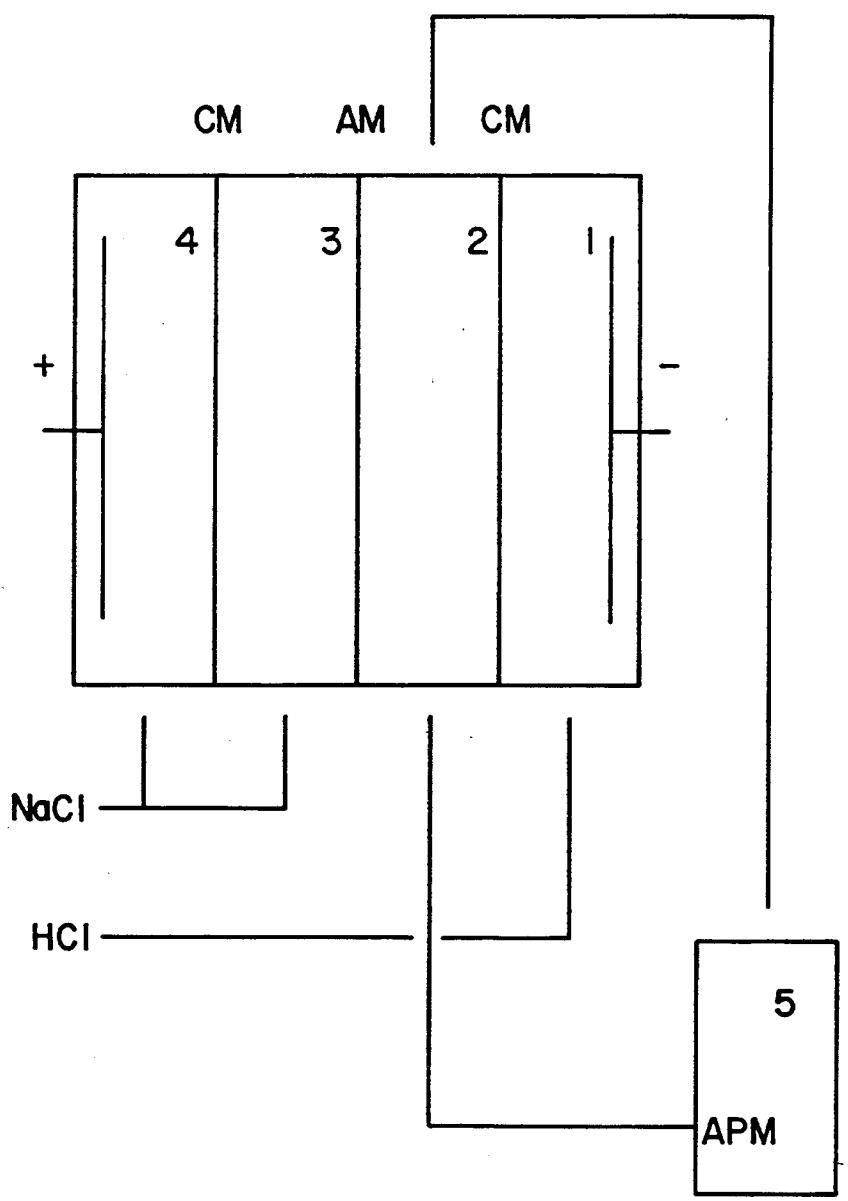
FIG. 3 is a schematic view of an electrodialyser provided with ion exchange membranes for removing $A_2PM$ from an aqueous APM solution.

In this example, A$_2$PM was removed from an aqueous APM solution by using an electrodialyser having four chambers partitioned with cation exchange membranes and anion exchange membranes, as shown in FIG. 3. As an anode, an electrode comprising an expanded Ti substrate covered with a noble metal oxide was used. As a cathode, a platinum electrode was used. A fluorine-containing cation exchange resin (Nafion 324, a trade mark by E. I. du Pont de Nemours & Co.) was used as the cation exchange membranes, and a fluorine-containing anion exchange membrane (SF-17, a trade mark by Tosoh Corporation) was used as the anion exchanger membranes. An aqueous 0.5N NaCl solution was introduced into an intermediate chamber 3 and an anode chamber 4, and an aqueous 0.2N HCl solution was introduced into a cathode chamber 1. By using a pump, 2.5 liters of an aqueous solution (60° C.) containing 3.7% of APM, 0.12% of DKP, 0.05% of AP and 240 ppm of A$_2$PM (A$_2$PM/APM=0.64%) was circulated through an intermediate chamber 2 for a period of 2 hours (this solution was prepared based on the results of Reference Example).

This operation was repeated 10 times, and the resulting solutions were combined to obtain about 25 liters of a solution containing 3.5% of APM, 0.08% of DKP, 0.03% of AP and 40 ppm of A$_2$PM (A$_2$PM/APM=0.11%). The combined solution was subjected to continuous crystallization in the same manner as in Example 1, to obtain a slurry having an average specific cake resistance of $4.5 \times 10^9$ m/kg.

COMPARATIVE EXAMPLE 8

The solution used in Example 7 (A$_2$PM/APM=0.64%, A$_2$PM=240 ppm) was subjected to continuous crystallization, without being subjected to the ion-exchange membrane treatment, to obtain a slurry having an average specific cake resistance of $12.5 \times 10^9$ m/kg.

EXAMPLE 8

A solution containing 5.0% of APM, 0.01% of DKP and 0.002% of AP but not containing A$_2$PM was subjected to continuous crystallization in the same manner as in Example 5, to obtain a slurry having an average specific cake resistance of $1.5 \times 10^9$ m/kg.

EXAMPLE 9

A solution containing 5.0% of APM, 0.05% of DKP, 0.03% of AP and 60 ppm of A$_2$PM (A$_2$PM/APM=0.12%) was subjected to continuous crystallization in the same manner as in Example 6, to obtain a slurry having an average specific cake resistance of $3.3 \times 10^9$ m/kg.

EXAMPLE 10

A solution containing 5.0% of APM, 0.10% of DKP, 0.06% of AP and 110 ppm of A$_2$PM (A$_2$PM/APM=0.22%) was subjected to continuous crystallization in the same manner as in Example 7, to obtain a slurry having an average specific cake resistance of $4.8 \times 10^9$ m/kg.

The results in Examples 1, 2, 5, 6 and 7 and Comparative Examples 1, 2, 3, 7 and 8 where the APM concentration was 3.5% are shown in Table 1 and FIG. 1.

TABLE 1

|  | APM (%) | A$_2$PM/APM (%) | Average Specific Cake Resistance (m/kg) |
| --- | --- | --- | --- |
| Example 1 | 3.5 | 0.35 | $11.5 \times 10^9$ |
| Example 2 | 3.5 | 0.60 | $12.3 \times 10^9$ |
| Example 5 | 3.5 | 0.00 | $2.1 \times 10^9$ |
| Example 6 | 3.5 | 0.17 | $8.3 \times 10^9$ |
| Example 7 | 3.5 | 0.11 | $4.5 \times 10^9$ |
| Comparative Example 1 | 3.5 | 0.80 | $12.7 \times 10^9$ |
| Comparative Example 2 | 3.5 | 1.10 | $13.8 \times 10^9$ |
| Comparative Example 3 | 3.5 | 1.50 | $13.9 \times 10^9$ |
| Comparative Example 7 | 3.5 | 0.69 | $13.1 \times 10^9$ |
| Comparative Example 8 | 3.5 | 0.64 | $12.5 \times 10^9$ |

The results in Examples 3, 4, 8, 9 and 10 and Comparative Examples 4, 5 and 6 where the APM concentration was 5.0% are shown in Table 2 and FIG. 2.

TABLE 2

|  | APM (%) | A$_2$PM/APM (%) | Average Specific Cake Resistivity (m/kg) |
| --- | --- | --- | --- |
| Example 3 | 5.0 | 0.35 | $5.6 \times 10^9$ |
| Example 4 | 5.0 | 0.60 | $8.0 \times 10^9$ |
| Example 8 | 5.0 | 0.00 | $1.5 \times 10^9$ |
| Example 9 | 5.0 | 0.12 | $3.3 \times 10^9$ |
| Example 10 | 5.0 | 0.22 | $4.8 \times 10^9$ |
| Comparative Example 4 | 5.0 | 0.80 | $8.5 \times 10^9$ |
| Comparative Example 5 | 5.0 | 1.10 | $8.6 \times 10^9$ |
| Comparative Example 6 | 5.0 | 1.50 | $9.7 \times 10^9$ |

EXAMPLE 11

Into a glass crystallization vessel (internal volume: 2,500 ml) equipped with an external cooling jacket and a stirrer, 2,000 ml of an aqueous solution (60° C.) containing 30 ppm of $A_2PM$ and 3.5% of APM was charged. While stirring at a tip speed of the stirrer blades of 2.3 m/sec., the temperature in the crystallization vessel was lowered at a rate of 5° C./10 min. by passing a cooling medium from an external water bath through the jacket. After the temperature in the crystallization vessel had reached 10° C., continuous crystallization was carried out in the following manner.

That is, the previously prepared aqueous APM solution containing 30 ppm of $A_2PM$ kept in an external constant temperature bath maintained at 60° C. was continuously fed into the crystallization vessel containing the previously prepared APM, which was maintained at 10° C. by means of a cooling medium, by a pump at such a rate that the residence time of the solution was 2 hours, and at the same time, the formed slurry was continuously discharged.

The filtration speed of the discharged slurry was determined by a leaf tester. As a result, it showed an almost constant value when the solution in the crystallization vessel had been substituted about 6 times or more. Thereafter, the continuous crystallization was continued, and the filtration speed was determined at the time when the solution in the crystallization vessel had been substituted 10 times. At this time, the determined filtration speed was 260 $l/m^2/min$.

In the subsequent examples, the filtration speed was determined at the time when the solution in the crystallization vessel had been substituted 10 times.

EXAMPLES 12 to 15

One mole of N-benzyloxycarbonyl-L-aspartic acid anhydride was reacted with 1 mole of APM in 300 g of acetic acid at room temperature for 24 hours, to obtain 290 g of N-benzyloxycarbonyl-L-aspartyl-L-aspartyl-L-phenylalaninemethyl ester (Z-$A_2PM$, $\alpha/\beta=4/1$).

The thus obtained Z-$A_2PM$ was catalytically reduced in methanol in the presence of a palladium-on-carbon catalyst in a customary manner. After the catalyst had been removed off by filtration, the methanol was distilled off to obtain 210 g of $A_2PM$ ($\alpha/\beta=4/1$).

Figure 5:
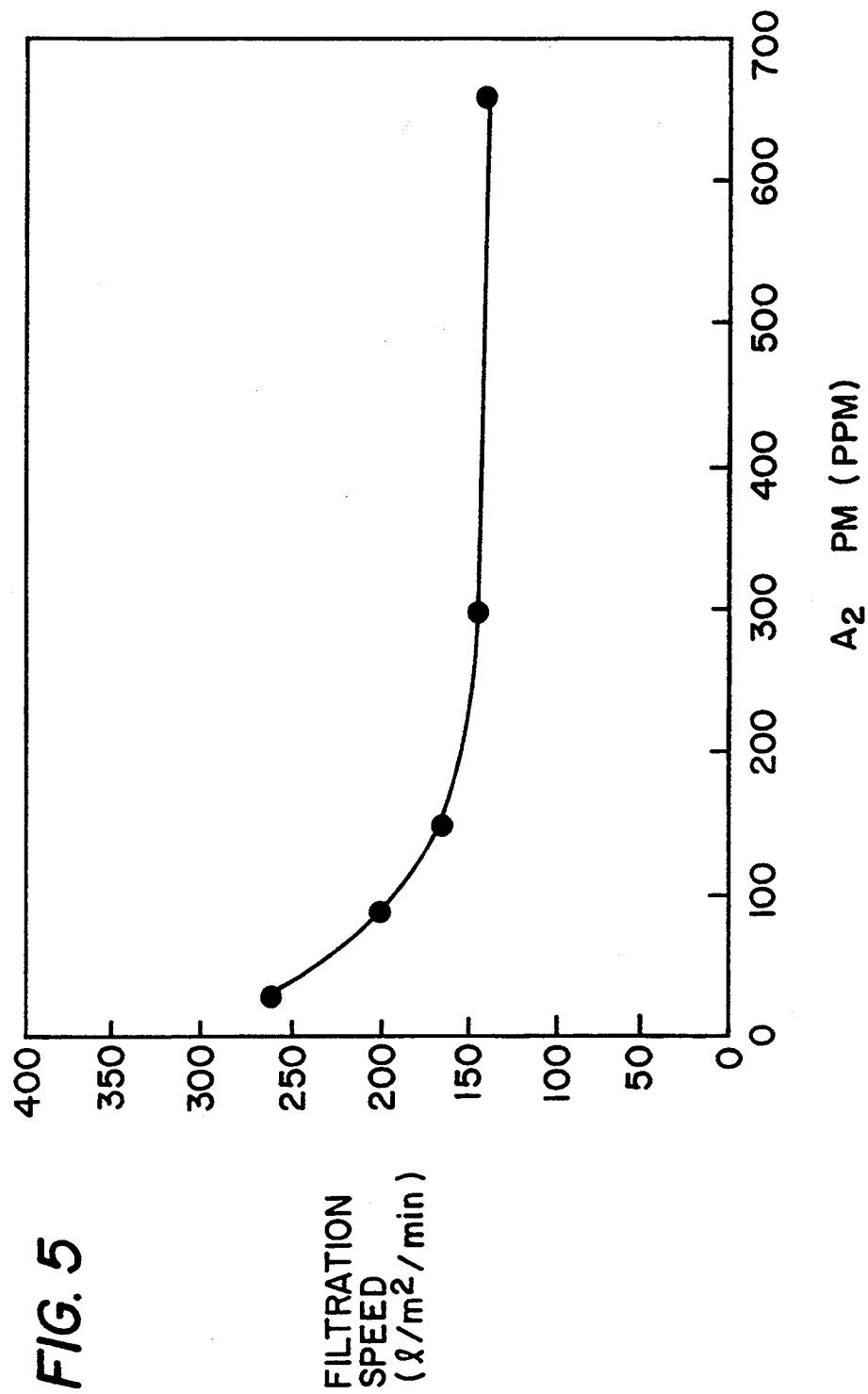
FIG. 5 is a graph showing the variation of the filtration speed with the content of $A_2PM$ in an aqueous APM solution.

The thus prepared $A_2PM$ was added to a hot aqueous solution containing 3.5% of APM, to prepare hot aqueous APM solutions containing a different amount of $A_2PM$. These solutions were subjected to continuous crystallization, and the filtration speed of the resulting slurries was determined, in the same manner as in Example 11. The results obtained are shown together with those in Example 11 in FIG. 5.

EXAMPLE 16

Into a glass cylindrical column (inner diameter: 80 mm) equipped with an external jacket, 5,000 ml of a strongly basic anion exchange resin of $Cl^-$ type (Amberlite IRA-410, a trade mark by Rohm & Hass Co.) was charged. While circulating hot water of 60° C. through the external jacket, 20 l of a solution (60° C.) containing 250 ppm of $A_2PM$, 3.6% of APM, 0.20% of DKP and 0.06% of AP (this solution was prepared based on the results of Reference Example) was passed downward through the column at a space velocity of 2.5 $hr^{-1}$, to obtain a solution containing 3.5% of APM, 0.05% of DKP, 0.03% of AP and 60 ppm of $A_2PM$.

The resulting solution was subjected to continuous crystallization in the same manner as in Example 11, to obtain a slurry having a filtration speed of 220 $l/m^2/min$. On the other hand, when the continuous crystallization was carried out without subjecting to the ion exchange resin treatment, the filtration speed was 150 $l/m^2/min$.

EXAMPLE 17

In this example, $A_2PM$ was removed from an aqueous APM solution by using an electrodialyser having four chambers partitioned with cation exchange membranes and anion exchange membranes, as shown in FIG. 3. As an anode, an electrode comprising an expanded Ti substrate covered with a noble metal oxide was used. As a cathode, a platinum electrode was used. A fluorine-containing cation exchange resin (Nafion 324, a trade mark by E. I. du Pont de Nemours & Co. ) was used as the cation exchange membrane, and a fluorine-containing anion exchange membrane (SF-17, a trade mark by Tosoh Corporation) was used as the anion exchanger membrane. An aqueous 0.5N NaCl solution was introduced into an intermediate chamber 3 and an anode chamber 4, and an aqueous 0.2N HCl solution was introduced into a cathode chamber 1. By using a pump, 2.5 liters of an aqueous solution (60° C.) containing 3.7% of APM, 0.12% of DKP, 0.05% of AP and 200 ppm of $A_2PM$ was circulated through an intermediate chamber 2 for a period of 2 hours (this solution was prepared based on the results of Reference Example).

This operation was repeated 10 times, and the resulting solutions were combined to obtain about 25 liters of a solution containing 3.5% of APM, 0.08% of DKP, 0.03% of AP and 40 ppm of $A_2PM$. The combined solution was subjected to continuous crystallization in the same manner as in Example 11, to obtain a slurry having a filtration speed of 260 $l/m^2/min$. On the other hand, when the continuous crystallization was carried out without subjecting to the ion exchange resin treatment, the filtration speed was 150 $l/m^2/min$.

REFERENCE EXAMPLE

Figure 4:
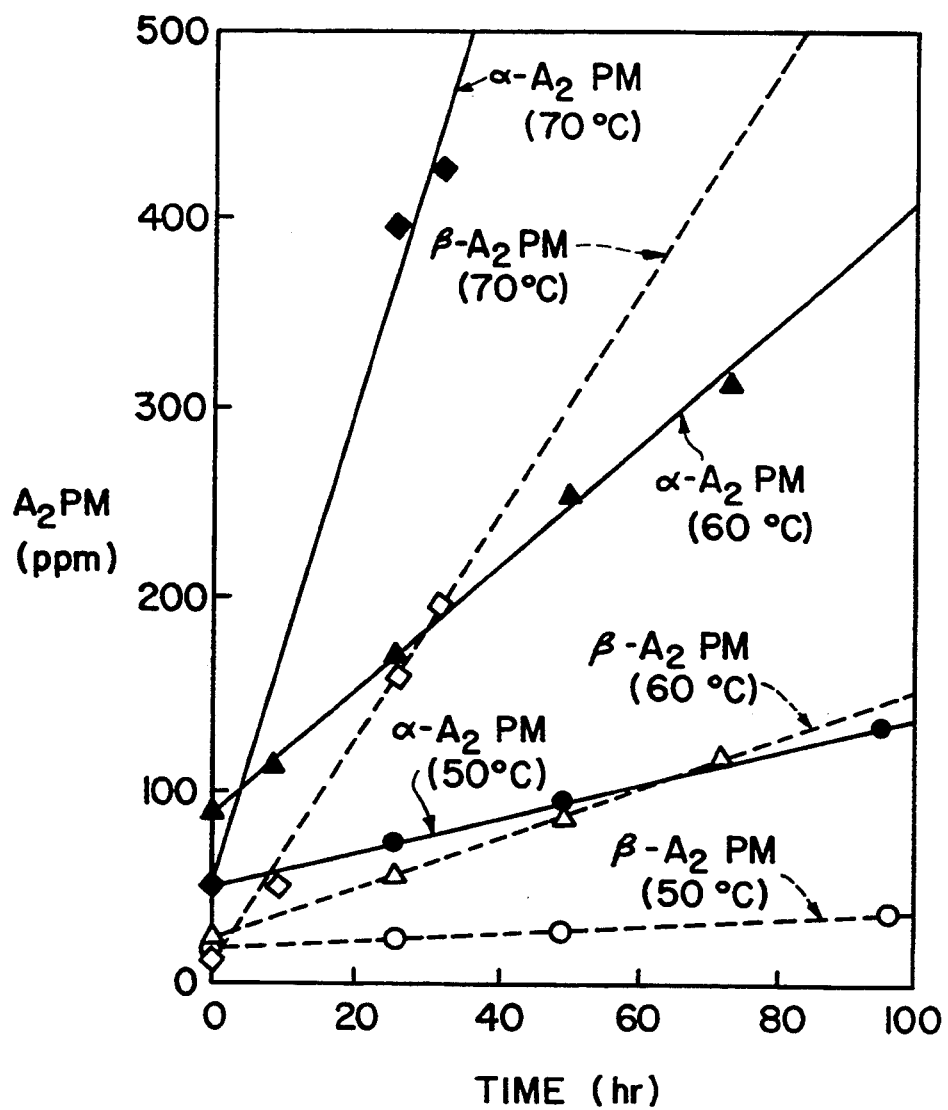
FIG. 4 is a graph showing the formation of $A_2PM$ in an aqueous APM solution at elevated temperatures.

An aqueous 3.5% APM solution was placed in a constant temperature bath of 50° C., 60° C. or 70° C., and the amount of $A_2PM$ formed was determined with the lapse of time. The results obtained are shown in FIG. 4.

According to this invention, there is provided an industrial process which is economically advantageous in the crystallization step and in subsequent steps, since APM crystals having good filtration and dehydration properties are be obtained. For example, equipment to be used in the solid-liquid separating step can be simplified, and the effectiveness of washing-off of impurities such as DKP contained in the mother liquor attached to APM crystals is markedly improved. With the improvement in dehydration properties, the drying load in the drying step is also reduced.

In this invention, since the cooling of APM-containing solution can be effected instantaneously in an already cooled crystallization vessel, the decomposition of APM is suppressed markedly, and a high-purity APM product is obtained.

In addition, according to this invention, the equipment can be made simple, and a markedly improved cooling efficiency is attained, as compared with the cooling by conductive heat transfer without forced flow.

Moreover, according to the method of this invention, the deposition of crystals on the heat transfer surface is small, and almost no scale is formed in the crystallization vessel. Thus, the decrease in cooling efficiency is minimized, and there is no nee for frequent troublesome descaling operations.

In the light of the above, this invention provides a highly useful industrial method of crystallization, which makes it possible to produce APM crystals having good filtration and dehydration properties while solving, e.g., the problem of fine crystals upon crystallization by cooling with forced flow and various problems encountered in the crystallization method without forced flow in which a "pseudo-solid phase" is formed.

While the invention has been described in detail and with reference to specific embodiments thereof, it will be apparent to one skilled in the art that various changes and modifications can be made therein without departing from the spirit and scope thereof.

What is claimed is:

1. A method for crystallizing α-L-aspartyl-L-phenylalanine methyl ester from a hot aqueous solution containing α-L-aspartyl-L-phenylalanine methyl ester by cooling, which comprises the steps of:
   (i) continuously supplying a hot aqueous solution of α-L-aspartyl-L-phenylalanine methyl ester to a crystallization vessel;
   (ii) monitoring the content of L-aspartyl-L-aspartyl-L-phenylalanine methyl esters in said solution and adjusting the concentration of said solution so that
   (a) the content of L-aspartyl-L-aspartyl-L-phenylalanine methyl esters is less than 0.6% by weight based on the weight of α-L-aspartyl-L-phenylalanine methyl ester in said solution, or (b) if the content of L-aspartyl-L-aspartyl-L-phenylalanine methyl esters is 0.6% by weight or more based on the weight of α-L-aspartyl-L-phenylalanine methyl ester in said solution, the concentration of L-aspartyl-L-aspartyl-L-phenylalanine methyl esters in said solution is adjusted to be 150 ppm by weight or less;
   (ii) lowering the temperature of said solution to at least a solubility temperature of α-L-aspartyl-L-phenylalanine methyl ester to thereby form a slurry; and
   (iii) continuously discharging the formed slurry from the crystallization vessel.

2. A method as in claim 1, wherein said solution is an aqueous solution obtained by purifying α-L-aspartyl-L-phenylalanine methyl ester containing, as impurities, L-aspartyl-L-aspartyl-L-phenylalanine methyl esters to a level where the content of the impurity is less than 0.6% by weight, based on the weight of α-L-aspartyl-L-phenylalanine methyl ester.

3. A method as in claim 2, wherein the content of L-aspartyl-L-aspartyl-L-phenylalanine methyl esters is 0.35% by weight or less based on the weight of α-L-aspartyl-L-phenylalanine methyl ester in said solution.

4. A method as in claim 2, wherein the crystallization is carried out under forced flow conditions.

5. A method as in claim 2, wherein the crystallization is carried out under mechanical stirring at a rate of from 0.5 to 5 m/sec in terms of the tip speed of stirrer blades.

6. A method as in claim 9, wherein the crystallization is carried out under mechanical stirring at a rate of from 1.0 to 4 m/sec in terms of the tip speed of stirrer blades.

7. A method as in claim 1, wherein the content of L-aspartyl-L-aspartyl-L-phenylalanine methyl esters is 0.35% by weight or less based on the weight of α-L-aspartyl-L-phenylalanine methyl ester in said solution.

8. A method as in claim 1, wherein the crystallization is carried out under forced flow conditions.

9. A method as in claim 5, wherein the crystallization is carried out under mechanical stirring at a rate of from 0.5 to 5 m/sec in terms of the tip speed of stirrer blades.

10. A method as in claim 7, wherein the crystallization is carried out under mechanical stirring at a rate of from 1.0 to 4 m/sec in terms of the tip speed of stirrer blades.

* * * * *